(12) United States Patent
Bacher et al.

(10) Patent No.: US 6,887,193 B2
(45) Date of Patent: May 3, 2005

(54) SEALING DEVICE FOR A RECTOSCOPE

(75) Inventors: Uwe Bacher, Tuttlingen (DE); Rainer Hermle, Gosheim (DE); Markus Salvermoser, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 208 days.

(21) Appl. No.: 10/304,821

(22) Filed: Nov. 26, 2002

(65) Prior Publication Data

US 2003/0144577 A1 Jul. 31, 2003

(30) Foreign Application Priority Data

Nov. 27, 2001 (EP) ............................................ 01710058

(51) Int. Cl.$^7$ ................................................ A61B 1/00
(52) U.S. Cl. ...................................................... 600/114
(58) Field of Search ................................ 600/114, 101, 600/159; 604/167.06

(56) References Cited

U.S. PATENT DOCUMENTS 5,779,697 A 7/1998 Glowa et al. ............... 606/185
6,117,070 A 9/2000 Akiba ......................... 600/154
6,458,077 B1 * 10/2002 Boebel et al. ............... 600/154

FOREIGN PATENT DOCUMENTS

EP 0 638 290 A1 2/1995
EP 0 696 459 A1 2/1996

* cited by examiner

*Primary Examiner*—Beverly M. Flanagan
(74) *Attorney, Agent, or Firm*—St. Onge Steward Johnston & Reens LLC

(57) ABSTRACT

The invention relates to a sealing device for a rectoscope for attaching on a sealing receiver of the rectoscope, and includes a sealing and an additional sealing element, where the sealing has a clip for securing to the sealing receiver of the rectoscope, an end surface with an aperture for introducing a medical instrument, and a sealing sleeve connecting the clip and the end surface to one another and where the end surface is mounted so as to be tiltable with respect to the rectoscope.

25 Claims, 4 Drawing Sheets

SEALING DEVICE FOR A RECTOSCOPE

Figure 1:
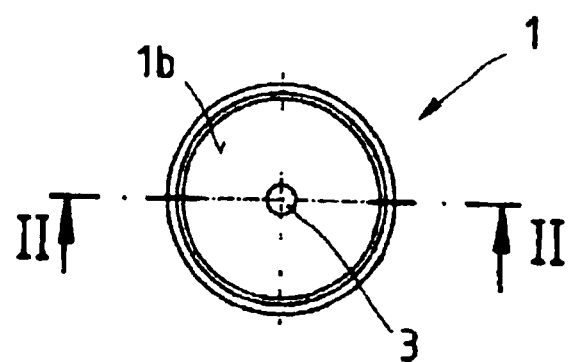

This application claims priority of pending European Patent Application 01 710 058.7 filed Nov. 27, 2001.

The invention relates to a sealing device for a rectoscope to be mounted on a sealing receiver of the rectoscope, which device includes a sealing and an additional sealing element.

In endoscopic examinations and/or endoscopic operations, medical instruments are introduced through the endoscope into the examination area. In order to prevent penetration of impurities into the endoscope and/or into the patient's body on the one hand, and on the other hand to avoid the escaping of air or gas pressure produced in the examination area in many procedures, sealings are used which have in their end surface an aperture for the passage of the medical instrument. Rigid sealings, however, have the disadvantage that the instrument introduced through the sealing is difficult to move in various radial directions.

Sealing devices of this kind are known, for instance, from U.S. Pat. No. 5,779,697. With rectoscopes used in proctoscopy, the rectoscope, unlike an endoscope, is not introduced into the patient's body by means of a trocar. Consequently a larger tilting angle is available for the medical instrument to be inserted into the rectoscope and a considerably greater tippable mobility must be ensured than is the case for sealing devices for endoscopes that are in general use.

It is accordingly the object of this invention to produce a sealing device of the aforementioned type, which allows the greatest possible room for maneuver for the medical instrument introduced through the aperture of the end surface, while ensuring a high level of sealing effectiveness.

This object of the invention is achieved by a sealing device for a rectoscope to be mounted on a sealing receiver of the rectoscope, which device includes a sealing and an additional sealing element, and where the sealing has a clip for attaching to the sealing receiver of the rectoscope, and end surface with an aperture for introducing a medical instrument, and a sealing housing that connects the clip and the end surface to one another and the end surface is mounted tiltably with respect to the rectoscope.

As a result of this invention's tiltably mobile mounting of the end surface with respect to the rectoscope, it is possible for the first time to configure the sealing device in such a way that the inserted medical instrument can be rotated without problems in various radial directions without any negative impact on the effectiveness of the sealing. To ensure that, if there is not a medical instrument inserted through the aperture of the sealing, the rectoscope is nevertheless sealed off, it is proposed with this device that an additional sealing element should be able to be secured to the sealing sleeve.

In a first practical embodiment of the invention, the sealing receiver, on which the inventive sealing device can be secured, is configured as a sealing sleeve.

The clip of the sealing is secured on the outside of the sealing sleeve, in one embodiment, by having the clip of the sealing overlap by at least one undercutting of the sealing sleeve.

In an additional embodiment of the invention it is proposed to secure the sealing clip on the inside of the sealing sleeve, and for this purpose the clip overlaps at least one projecting part mounted on the interior of the sealing sleeve.

According to a first practical embodiment of the invention, the tiltably movable mounting of the end surface is achieved by the fact that the sealing housing is configured as a concertina having at least one pleat. Because the configuration of the pleats in the sealing housing produces the sealing's tiltable mobility, the tilting of the sealing also has no influence on the tightness of the aperture in the end surface, and thus the motion of the medical instrument does not affect the tightness. In addition to the horizontal positioning of the at least one pleat, it is also possible to configure the concertina in such a way that the at least one pleat is formed in a spiral shape encircling in the material of the sealing housing.

The tiltable mobility of the sealing can be varied through the configuration of more pleats and various pleat heights. Depending on the procedure, the pleats of a concertina in extended state can all have the same height, or else at least individual pleats of the concertina in the extended state can have a height different from the other pleats.

According to a second embodiment of the invention, to prepare the tiltably movable mounting of the end surface it is proposed that the sealing housing forming at least one regulating bend position should have an area with a reduced wall strength on at least one prescribed location, so that during a tilting motion of the medical instrument mounted in the aperture of the end surface, the area with a reduced wall strength can buckle inward in order to ensure the tilting of the end surface.

The tiltable mobility of the sealing in this embodiment can be varied because several areas in the material of the sealing housing are formed with reduced wall strength, so that these areas with reduced wall strength are mounted so as to be displaced with respect to one another vertically and/or by the scope of the sealing housing. It is also proposed through this invention that in addition to the configuration of individual areas separate from one another, the at least one area with reduced wall strength should be configured as a horizontally surrounding area or as a spiral-shaped surrounding area in the material of the sealing housing.

In a third embodiment of the invention, the tiltable mobility of the end surface of the sealing is achieved indirectly, by having the sealing receiver, on which the sealing is secured by the sealing clip, mounted so as to be tiltable in relation to the rectoscope.

The mounting of the sealing receiver is made tiltably mobile, in one embodiment of the invention, because the sealing receiver is configured as a spherical-shaped element or spherical-section-shaped element inserted into an aperture of the rectoscope and this element has an aperture for the passage of a medical instrument. In this mounting, which is simple and not costly to manufacture, the sealing receiver functions almost as a ball joint.

In an additional embodiment of the invention, the sealing receiver is connected by a Cardan mounting in an aperture of the endoscope.

To ensure, in the tiltable mounting of the sealing receiver, that the rectoscope is also sealed completely tight in the area of the sealing receiver mounted in the aperture of the rectoscope, it is further proposed that the sealing receiver is sealed by means of an additional sealing element, in particular an O-ring, with respect to the aperture in the end surface of the rectoscope.

To ensure further, especially in the configuration of the sealing housing as a concertina, that, when the medical instrument is withdrawn from the aperture in the end surface or when the sealing is tilted by means of the medical instrument, the sealing housing is excessively elongated in the axial direction, it is proposed through this invention that the extension of the sealing housing in the axial direction should be restrictable. This axial extension can be restricted by having the clip and the end surface connected to one another by means of at least one non-elongatable restricting element, in particular a rope. If several restricting elements are used, it is advantageous if they are arranged uniformly around the aperture for the passage of the medical instrument.

The aperture in the end surface of the sealing can be securely sealed off from the medical instrument if the diameter of the aperture is smaller than the diameter of the medical instrument that is to be received.

The tiltable mobility of the medical instrument mounted in the aperture of the end surface can be improved if the rim of the end surface, which surrounds the aperture in the end surface, is semicircular in cross-section, so that there is an almost exclusively linear-shaped sealing positioning of the rim of the aperture on the medical instrument. In comparison to a simple cylindrical configuration of this rim, the semicircular shape allows a slight, low-resistance swiveling of the medical instrument.

In a practical embodiment of the invention's sealing device, the additional sealing element is a cross-slitted sealing. Use of this known cross-slitted sealing guarantees a secure sealing when the medical instrument is removed, since in this case the areas of the end surface of the cross-slitted sealing, which are separated from one another by the cross-slit, are in sealing contact with one another because of the return force of the material. In place of the cross-slitted sealing, other sealing elements such as valves or release joints may be used.

Finally, in a preferred embodiment of the invention, it is proposed that the sealing can be secured on the distal side on a distal end surface of the rectoscope and the additional sealing element can be secured on the proximal side on the distal end surface of the rectoscope.

Additional characteristics and advantages of the invention are presented by means of the description of the related illustrations, in which the six embodiments of an inventive sealing are presented schematically by way of example. The illustrations are as follows:

FIG. 1 View from above of an initial embodiment of an inventive sealing.

Figure 2:
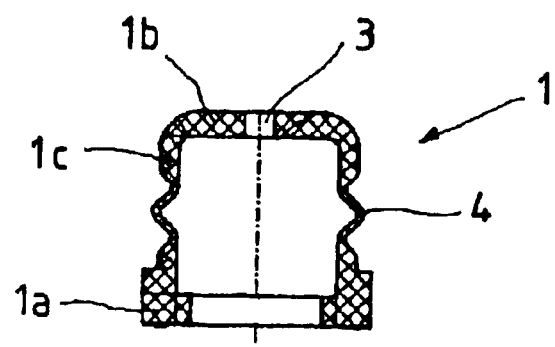

FIG. 2 Longitudinal section along the intersection line II–II in accordance with FIG. 1.

Figure 3:
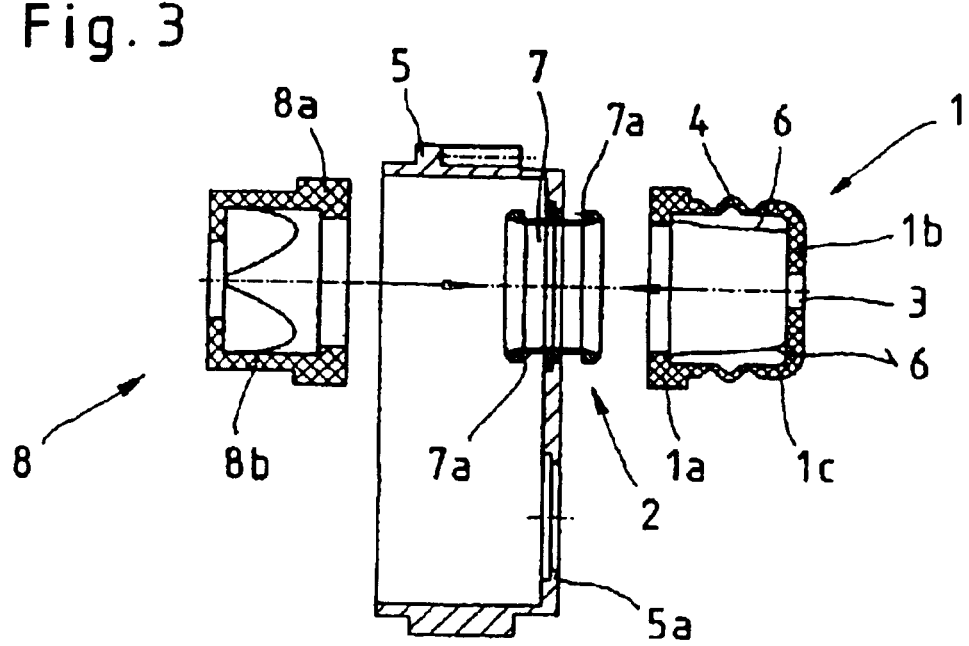

FIG. 3 Schematic longitudinal section through an inventive sealing device, depicting a second embodiment of an inventive sealing.

Figure 4A:
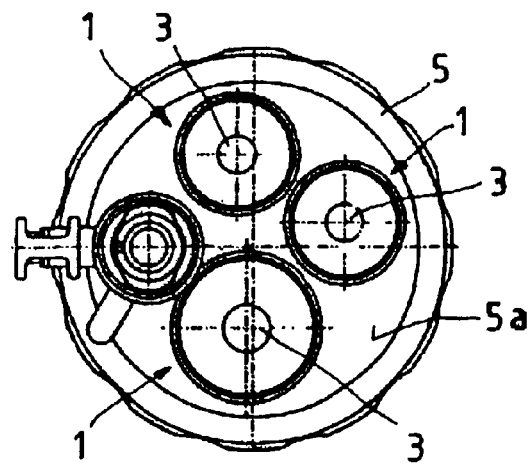

FIG. 4a View from above of a sealing device in accordance with FIG. 3 in assembled condition.

Figure 4B:
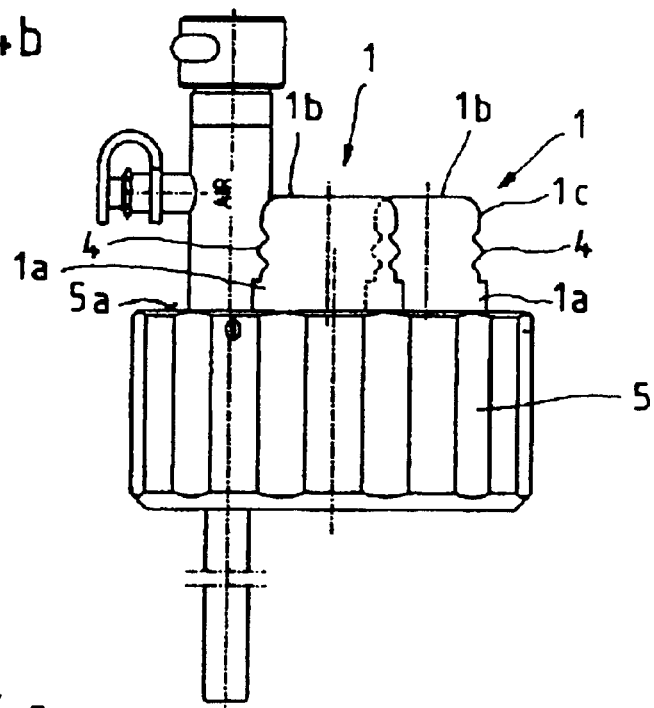

FIG. 4b Side view of the sealing device in accordance with FIG. 4a.

Figure 4C:
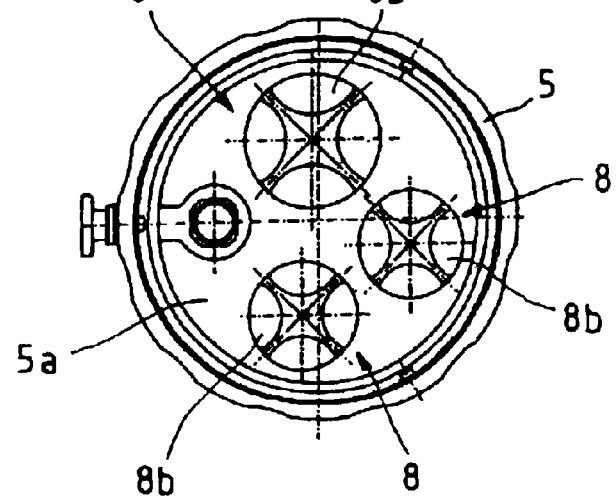

FIG. 4c View from below of the sealing device in accordance with FIGS. 4a and 4b.

Figure 5:
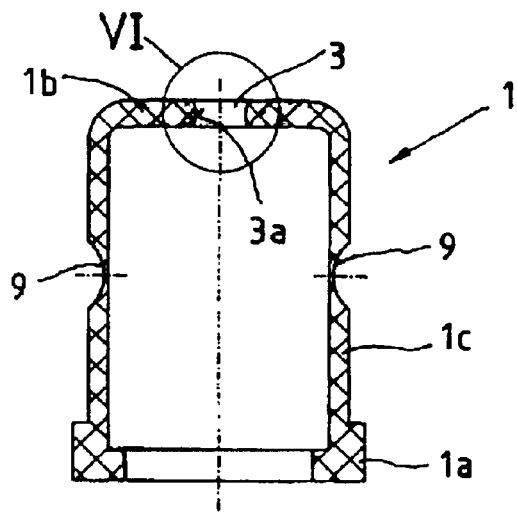

FIG. 5 Longitudinal section through a third embodiment of an inventive sealing.

Figure 6:
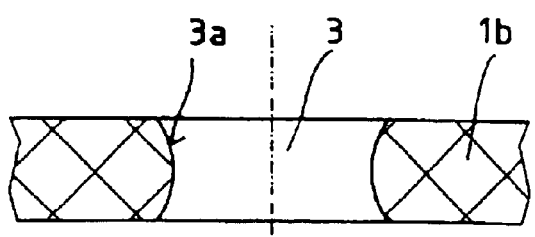

FIG. 6 Enlarged view of detail VI from FIG. 5.

Figure 7:
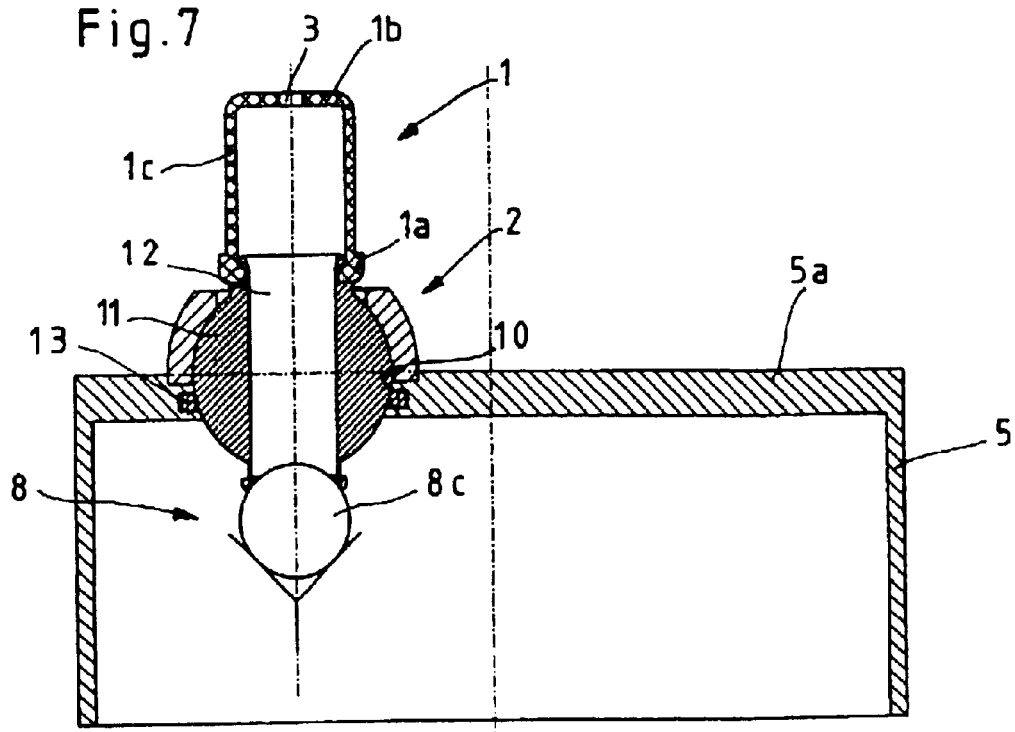

FIG. 7 Schematic longitudinal section through a fourth embodiment of an inventive sealing.

Figure 8:
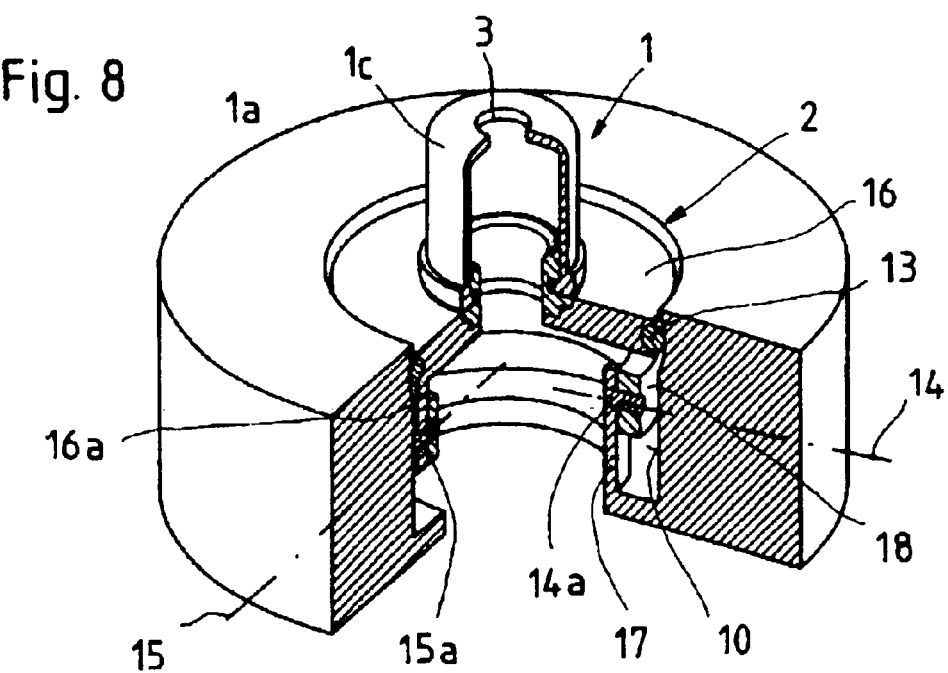

FIG. 8 Schematic perspective and partially cut-out view of a fifth embodiment of an inventive sealing.

Figure 9:
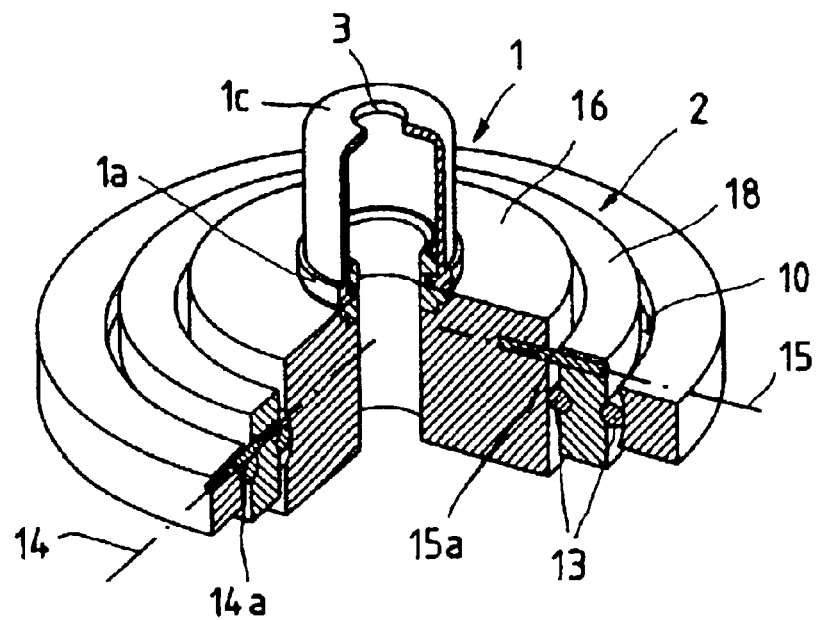

FIG. 9 View corresponding to FIG. 8, showing a sixth embodiment.

The sealings 1 depicted in FIGS. 1 and 9 consist of a clip 1a for securing the sealing 1 to a sealing receiver 2 of an rectoscope, an end surface 1b, and a sealing housing 1c connecting the clip 1a with the end surface 1b. As can be further seen from the illustrations, an aperture is made in the end surface 1b. In the use of the sealing 1 on a rectoscope, the aperture 3 serves as a passageway for a medical instrument.

To ensure effective sealing between the medical instrument to be introduced and the aperture 3 in the end surface 1b, the diameter of the aperture 3 is determined so that it is slightly smaller than the diameter of the medical instrument to be inserted. On the basis of the material elasticity of the sealing 1, which is preferably produced out of a rubber material, the rim 3a of the aperture 3 presses firmly and securely against the medical instrument.

In the embodiments depicted in FIGS. 1 to 4c, the sealing housing 1c of the sealing 1 is configured as a concertina having only one pleat 4. By means of the pleat formation of the sealing housing 1c, the sealing housing 1c becomes malleable, that is, capable of being elongated and pressed in as well as tiltable. The malleability of the sealing housing 1c is advantageous because in this way the medical instrument inserted through the aperture 3 of the end surface 1b during an examination can be easily moved in various radial directions, without the material of the sealing 1 affecting this tiltable mobility.

In addition to the configuration of the concertina with just a single pleat 4, it is also possible of course to provide several pleats 4, which are constructed of the material of the sealing housing 1c and are arranged horizontally or spirally. The malleability and thus the tiltable mobility increase along with the number of pleats. In addition to the number of pleats 4, the tiltability of the sealing 1 can be influenced by the height of the individual pleats 4. In the simplest case all pleats 4 of the concertina have the same height when extended. However, it is also possible to configure at least one pleat 4 with a height, when extended that differs from that of the other pleats 4.

FIG. 3 shows a second embodiment of the sealing 1, whose sealing housing 1c is configured as a concertina, in a sealing mount for mounting on a distal side terminal cap 5 of a rectoscope. The embodiment of FIG. 3 differs from the first embodiment of the sealing 1 shown in FIG. 2 in that the clip 1a and the end surface 1b of the sealing 1 are connected to one another by means of at least one non-elongatable restricting element 6, preferably a rope.

The restricting element 6 serves to prevent any overelongation of the sealing housing 1c, which can result in destruction and thus permeability of the sealing housing 1c. This restricting of the axial elongation of the concertina is essential, particularly upon withdrawing the medical instrument from the aperture 3 of the end surface 1b and in extreme tilting motions of the medical instrument. Especially for restricting the lengthwise elongation in extreme tilting motions, it can be advantageous if several, such as three, restricting elements 6 are distributed around the aperture 3.

To secure the sealing 1 on the terminal cap 5, in the illustrated embodiment, the sealing receiver 2 of the terminal cap 5 is configured as a sealing sleeve 7. When mounted, the clip 1a of the sealing overlaps by one undercutting 7a of the sealing sleeve 7 and thus secures the sealing 1 to the rectoscope. To ensure that the rectoscope is also tightly secure even when no medical instrument is installed in the sealing 1, the sealing device has an additional sealing element 8, which, coming from the proximal side, is affixed on the sealing sleeve 7 of the distal end surface 5a. This additional sealing element 8, which is configured as a cross-slit sealing 8b in the illustrated embodiment, is also secured by a clip 8a to an undercutting 7a of the sealing sleeve 7.

In addition to this illustrated securing of the clip 1a of the sealing 1 on the outside of the sealing sleeve 7, it is of course also possible to secure the clip 1a on the interior of the sealing sleeve 7. In this case, on the inside of the sealing sleeve 7 at least one projection is mounted jutting inward, which the clip 1a of the sealing 1 secures and undercuts. It is likewise possible to configure the additional sealing element 8, for instance, as a return cap or as a valve 8c, as is illustrated in FIG. 7.

The illustrations of FIGS. 4a to 4c show a sealing device corresponding in theory to FIG. 3. As can be seen from these illustrations, several concertina sealings 1 can be secured on the terminal cap 5.

In the third configuration of the sealing 1 illustrated in FIG. 5, the end surface 1b of the sealing 1 relative to the rectoscope is made tiltably mobile by the fact that at least one area forming a regulatory notch with a reduced wall thickness 9 is formed in the material of the sealing housing 1c on a predetermined spot. In a similar way as in the formation of the pleats 4 of the concertina, the malleability of the sealing 1 can vary with the number and/or arrangement of the areas with a reduced wall thickness 9 toward one another. In the embodiment illustrated in FIG. 5, the area with a reduced wall thickness 9 is configured as a horizontally surrounding area in the material of the sealing housing 1c.

In alternative embodiments, these areas with a reduced wall thickness 9 can also be formed as individual partial areas arranged at intervals from one another and/or staggered or as a spirally shaped surrounding area in the material of the sealing housing 1c.

The enlarged detail, seen in FIG. 6, from FIG. 5 shows how the rim 3a of the end surface 1b surrounding the aperture 3 for inserting the medical instrument can be configured in order to mount the medical instrument so that it is especially tiltably mobile. The rim 3a formed as a semicircle in cross-section in this embodiment results in an almost linear-shaped closely formed position against the medical instrument inserted into the aperture 3. Because of this purely linear-shaped contact, the instrument is mounted in an especially tiltable way in the aperture 3, because in rotating the instrument, almost no material resistances of the sealing material need to be overcome. The illustrated configuration of the rim 3a is of course usable in all embodiments illustrated in FIGS. 1 to 8.

Shown in FIGS. 7 to 9 are three additional embodiments indicating how the end surface 1b of the sealing 1 can be mounted rotatably with respect to the rectoscope. In these designs of the sealing 1, tilting is achieved indirectly, that is, by having the sealing receiver 2, on which the clip 1a of the sealing 1 is secured, tiltably mounted with respect to the rectoscope.

According to the fourth embodiment, shown in FIG. 7, the tiltably mobile mounting of the sealing receiver 2 is achieved through the fact that the sealing receiver 2 is configured as a spherical-shaped element 11 that can be inserted into an aperture 10 of the rectoscope, and this element allows swiveling of the medical instrument inserted into the sealing 1 in the manner of a ball joint. In the illustrated embodiment, the clip 1a of the sealing 1 is not secured directly on the spherical element 11 but rather on a sleeve 12 inserted into the spherical element 11 and combining with it to form the sealing receiver 2. However, it is also possible, of course, to secure the clip 1a of the sealing 1 directly on the spherical element 11.

An additional tiltable way of mounting the sealing receiver 2, which is comparable to the configuration according to FIG. 7, is possible if the sealing receiver 2 is designed not as a completely spherical element 11 but instead only as a spherical-segment-shaped element, so that the sphere segment preferably a segment surrounding the middle area of a sphere in order to prevent any slipping out of the aperture in the end surface of the rectoscope.

To ensure that, even when the sealing receiver 2 mounted tiltably in the aperture 10 of the rectoscope is used, the rectoscope is completely and reliably sealed, the spherical element 11 according to the embodiment in FIG. 7 is sealed with respect to the rim of the aperture 10 by means of a sealing in the form for instance of an O-ring 13.

The illustrations in FIGS. 8 and 9, finally, show fifth and sixth embodiments of the sealing 1, which resemble the embodiment of FIG. 7 in that the sealing receiver 2 is mounted to be tiltably mobile in the aperture 10 of the rectoscope, in order to allow rotation of the end surface 1b of the sealing 1 with respect to the rectoscope. In the embodiments of FIGS. 8 and 9, the sealing receiver 2 connected by a Cardan mounting in each case in the aperture 10 of the rectoscope.

As can be seen from the theoretical sketches according to FIGS. 8 and 9, the sealing receiver 2 is configured as a disk 16 that is tiltable around two rotation axes 14 and 15, and this disk is mounted in the aperture 10 of the rectoscope.

To form the Cardan mounting, in the first embodiment shown in FIG. 8 of a Cardan mounting of the sealing receiver 2, two carrier arms 17 are arranged on the rim of the aperture 10 of the rectoscope, which arms bear a swivel frame 18 that can be tilted around the first swivel axis 14 by means of axle necks 14a. By means of two mounting links 16a and axle neck 15a, the tiltable disk 16 can be mounted tiltably around the second swivel axis 15 on the swivel frame 18, so that the two swivel axes 14 and 15 are arranged at a 90 degree angle to one another.

The tiltable disk 16 is sealed off with respect to the aperture 10 of the rectoscope in this embodiment by means of an O-ring 13, where the O-ring 13 is mounted on the tiltable disk 16 and the sealing surface of the aperture 10 is preferably concave in shape in order to facilitate swiveling of the tiltable disk 16. It is also possible, of course, to mount the O-ring 13 in the aperture 10 and to configure the radial outer surface of the tiltable disk 16, which forms the sealing surface in a concave shape.

In the second embodiment of a Cardan mounted sealing receiver 2, shown in FIG. 9, the tiltable disk 16 and the swivel frame 18 are arranged concentrically with respect to one another in the aperture 10 of the rectoscope. As can be seen from the schematic illustration, in this embodiment the swivel frame 18 is mounted directly over the axle neck 14a in the aperture 10 in the end surface of the rectoscope so that it can swivel. The tiltable disk 16, in turn, is arranged within the swivel frame 18 and mounted so that it can swivel over the axle neck 15a in the swivel frame 18. In this embodiment as well, the swivel axes 14 and 15 are mounted at a 90-degree angle to one another.

In order to ensure that the rectoscope is also completely and reliably sealed off in this sealing receiver 2 that is in a Cardan mounting in the aperture 10 of the rectoscope, in the embodiment of FIG. 9 the tiltable disk 16, on the one hand, is sealed off with respect to the swivel frame 18 and, on the other hand, the swivel frame 18 is sealed off with respect to the rim of the aperture 10 of the rectoscope by sealings configured for instance as O-rings. 13. As can be seen from the illustration, the O-rings 13 are mounted on the swivel frame 18 and the sealing surfaces on the rim of the aperture 10 of the rectoscope on the one hand, and on the tiltable disk 16 on the other hand, with which the O-rings 13 are in tight contact, are level in the related area close to the axes, whereas they are increasingly concave-shaped in the remote areas proceeding from the axle necks 14a and 15a, in order to be able to pick up the movement of the O-rings 13 describing a circle segment on the tiltable disk 16 or on the swivel frame 18.

Alternatively, the sealing between the aperture 10 and the swivel frame 18 can also be configured in such a way that the O-rings 13 are mounted in the aperture 10 on the one hand and on the tiltable disk 16 on the other hand. The corresponding sealing surfaces on the swivel frame 18 are then configured in such a way as to be level in the related areas close to the axes and increasingly concave in the remote areas proceeding from the axle necks 14a and 15a.

Sealings 1 or sealing devices of this type, according to FIGS. 1 to 9, are distinguished in that they reserve sufficient room for maneuvering for the medical instrument introduced through the aperture 3 of the end surface 1b on the one hand, and ensure reliable sealing on the other hand.

Reference Numbers to Illustrations
1 Sealing
1a Clip
1b End surface
1c Sealing housing
2 Sealing receiver
3 Aperture
3a Rim
4 Pleat
5 Terminal cap
5a Distal end surface
6 Restricting element
7 Sealing sleeve
7a Undercutting
8 Sealing element
8a Clip
8b Cross-slit sealing
8c Valve
9 Area with reduced wall thickness
10 Aperture
11 Spherical element
12 Sleeve
13 O-ring
14 Swivel axis
14a Axle neck
15 Swivel axis
15a Axle neck
16 Tiltable disk
16a Mounting link
17 Carrier arm
18 Swivel frame

What is claimed is:

1. A sealing device for a rectoscope to be mounted on a sealing receiver of the rectoscope, which device has a sealing and an additional sealing element and where the sealing includes a clip for securing to the sealing receiver of the rectoscope, an end surface with an aperture for introducing a medical instrument, as well as a sealing housing that connects the clip and the end surface to one another and where the end surface is mounted so as to be tiltable with respect to the rectoscope, distinguished in that the sealing housing is configured as a concertina having at least one pleat.

2. A sealing device according to claim 1, distinguished in that the sealing receiver is configured as a sealing sleeve.

3. A sealing device according to claim 2, distinguished in that the clip of the sealing can be secured on the outside of the sealing sleeve overlapping by at least one undercutting of the sealing sleeve.

4. A sealing device according to claim 2, distinguished in that the clip of the sealing can be secured on the interior of the sealing sleeve so that the clip overlaps by at least one undercut on the inside of the sealing sleeve.

5. A sealing device according to claim 4, distinguished in that the sealing housing has at least one regulatory notch forming an area with reduced wall thickness on at least one predetermined spot.

6. A sealing device according to claim 5, distinguished in that several areas with reduced wall thickness are configured in the material of the sealing housing, where these areas with reduced wall thickness are arranged so as to be offset from one another in height and/or over the area of the sealing housing.

7. A sealing device according to claim 5, distinguished in that the at least one area with reduced wall thickness is configured as a horizontally surrounding area in the material of the sealing housing.

8. A sealing device according to claim 5, distinguished in that the at least one area with reduced wall thickness is configured as a spiral-shaped surrounding area in the material of the sealing housing.

9. A sealing device according to claim 1, distinguished in that the at least one pleat is configured in surrounding spiral shape in the material of the sealing housing.

10. A sealing device according to claim 1, distinguished in that the concertina has several pleats.

11. A sealing device according to claim 10, distinguished in that all pleats when extended have the same height.

12. A sealing device according to claim 10, distinguished in that at least individual pleats when extended have a height different from the other pleats.

13. A sealing device according to claim 1, distinguished in that the sealing receiver is mounted to be tiltable with respect to the rectoscope.

14. A sealing device according to claim 13, distinguished in that the sealing receiver is configured as a spherical-shaped element or spherical-section-shaped element inserted into an aperture of the rectoscope, which element has an aperture for introducing a medical instrument.

15. A sealing device according to claim 13, distinguished in that the sealing receiver is connected by a Cardan mounting in an aperture of the rectoscope.

16. A sealing device according to claim 15, distinguished in that the sealing receiver is securely sealed by means of an additional sealing element, especially an O-ring, with respect to the aperture of the rectoscope.

17. A sealing device according to claim 16, distinguished in that the extension of the sealing housing in the axial direction can be restricted.

18. A sealing device according to claim 17, distinguished in that the clip and the end surface are connected to one another by means of at least one non-elongatable restricting element.

19. A sealing device according to claim 18, distinguished in that the restricting element is evenly arranged around the aperture for introducing a medical instrument.

20. A sealing device according to claim 18, distinguished in that the restricting element is configured as a rope.

21. A sealing device according to claim 20, distinguished in that the diameter of the aperture in the end surface is smaller than the diameter of the medical instrument to be introduced.

22. A sealing device according to claim 21, distinguished in that a rim surrounding the aperture in the end surface is configured as semicircular in cross-section.

23. A sealing device according to claim 22, distinguished in that the additional sealing element is a cross-slit sealing.

24. A sealing device according to claim 22, distinguished in that the additional sealing element is configured as a valve or return cap.

25. A sealing device according to claim 24, distinguished in that the sealing can be secured on the distal side on a distal end surface of the endoscope and the additional sealing element can be secured on the proximal side on the distal end surface of the rectoscope.

* * * * *